United States Patent
Blomqvist et al.

(10) Patent No.: US 11,517,267 B2
(45) Date of Patent: Dec. 6, 2022

(54) DETECTOR ARRANGEMENT SUITED FOR OPTICAL SENSORS

(71) Applicant: Nokia Technologies Oy, Espoo (FI)

(72) Inventors: Kim Blomqvist, Espoo (FI); Leo Karkkainen, Helsinki (FI); David Bitauld, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 276 days.

(21) Appl. No.: 16/771,126

(22) PCT Filed: Nov. 16, 2018

(86) PCT No.: PCT/EP2018/081506
§ 371 (c)(1),
(2) Date: Jun. 9, 2020

(87) PCT Pub. No.: WO2019/120794
PCT Pub. Date: Jun. 27, 2019

(65) Prior Publication Data
US 2021/0161473 A1    Jun. 3, 2021

(30) Foreign Application Priority Data
Dec. 22, 2017   (EP) .................................... 17210106

(51) Int. Cl.
*A61B 5/1455*   (2006.01)
*A61B 5/024*    (2006.01)
*A61B 5/00*     (2006.01)

(52) U.S. Cl.
CPC ........ *A61B 5/7214* (2013.01); *A61B 5/02427* (2013.01); *A61B 5/14552* (2013.01); *A61B 5/6802* (2013.01); *A61B 2562/0233* (2013.01)

(58) Field of Classification Search
CPC .............. A61B 5/1455; A61B 5/14552; A61B 5/02427; A61B 5/6802; A61B 2562/0233
See application file for complete search history.

(56) References Cited

U.S. PATENT DOCUMENTS

| | | | |
|---|---|---|---|
| 8,649,836 B2 * | 2/2014 | Shimizu ............. | A61B 5/14532 600/316 |
| 8,818,473 B2 * | 8/2014 | McKenna .......... | A61B 5/14551 600/323 |
| 2013/0060104 A1 | 3/2013 | Schlottau ...................... | 600/310 |
| 2017/0055907 A1 | 3/2017 | Altebaeumer et al. | |

FOREIGN PATENT DOCUMENTS

| | | | |
|---|---|---|---|
| EP | 3 087 916 A1 | 11/2016 | |
| EP | 3 162 285 A1 | 5/2017 | |

\* cited by examiner

*Primary Examiner* — Eric F Winakur
(74) *Attorney, Agent, or Firm* — Harrington & Smith

(57) ABSTRACT

An apparatus with a first photodetector and a second photodetector is provided. The apparatus is configured to receive light, and the first photodetector is configured to detect a first portion of the light. The first photodetector and the second photodetector are in a stacked arrangement and the apparatus is configured to pass a second portion of the light through the first photodetector to the second photodetector. The apparatus further includes an optical blocking filter configured to filter the second portion of the light prior to the second portion of the light arriving at the second photodetector.

14 Claims, 6 Drawing Sheets

DETECTOR ARRANGEMENT SUITED FOR OPTICAL SENSORS

CROSS REFERENCE TO RELATED APPLICATION

This patent application is a U.S. National Stage application of International Patent Application Number PCT/EP2018/081506 filed Nov. 16, 2018, which is hereby incorporated by reference in its entirety, and claims priority to EP 17210106.5 filed Dec. 22, 2017.

TECHNICAL FIELD

The present application generally relates to a detector arrangement suited for optical sensors. Some example embodiments are suited for physiological measurement sensors.

BACKGROUND

This section illustrates useful background information without admission of any technique described herein representative of the state of the art.

Various measurement devices that measure physiological parameters of a subject such as pulse sensors can be used for measuring heart rate, movements or other personal parameters. The measurements can be performed for example by using a sensor device in a chest strap that is worn under clothes or by using a wrist worn watch-like sensor device.

Heart rate can be monitored for example optically using a photoplethysmogram (PPG) sensor. Such optical heart rate measurement is sensitive to movements. Motion artifacts caused by movements may corrupt the pulsatile heart rate (HR) signal and may confuse the HR monitoring algorithms of the sensor. The end result is that the calculated HR in beats per minute (BPM) may be wrong.

However, keeping the sensor completely stably on the wrist is difficult in practice. For example, the wrist strap cannot be kept too tight, because it would be unpleasant for the user and might even stop or deteriorate blood circulation in small vessels thereby causing the measurement signal to disappear. Also movements of the subject wearing the sensor may cause motion artifacts. Therefore motion artifacts cannot be completely avoided.

In addition to PPG sensors, motion artifacts may exist also in other optical sensors used for physiological measurements.

SUMMARY

Various aspects of examples are set out in the claims.

According to a first example aspect of the present invention, there is provided an apparatus comprising:
- a first photodetector and a second photodetector, wherein the apparatus is configured to receive light,
- the first photodetector is configured to detect a first portion of the light, and
- the first photodetector and the second photodetector are in a stacked arrangement and the apparatus is configured to pass a second portion of the light through the first photodetector to the second photodetector, the apparatus comprising
- an optical blocking filter configured to filter the second portion of the light prior to the second portion of the light arriving at the second photodetector.

For the sake of clarity it is noted that the optical blocking filter is positioned such that it filters light that has been passed through the first photodetector. In other words, the first portion of light is not filtered by the optical blocking filter.

In an example embodiment, magnitudes of the first and second portions of light are substantially equal.

In an example embodiment, the second portion is 45-55% of light incident on the first photodetector.

In an example embodiment, the first photodetector comprises semi-transparent material.

In an example embodiment, the first photodetector comprises holes, which allow the second portion of the light to pass through the first photodetector.

In an example embodiment, the apparatus is configured to pass the second portion of light through the first photodetector without changing direction of the light.

In an example embodiment, the optical blocking filter is a notch filter. In another example embodiment, the optical blocking filter comprises a dichroic mirror.

In an example embodiment, the apparatus is configured to detect a target wavelength, and the optical blocking filter is configured to block the target wavelength.

In an example embodiment, the apparatus further comprises a light source configured to emit light at a target wavelength, and the optical blocking filter is configured to block the target wavelength.

In an example embodiment, the apparatus comprises more than one optical blocking filter in a stacked arrangement.

In an example embodiment, the apparatus further comprises an angle adjustment element configured to adjust the angle of incidence of the light prior to the light being split by the optical arrangement.

In an example embodiment, the apparatus further comprises analog circuitry configured to subtract an output signal of the second photodetector from an output signal of the first photodetector.

In an example embodiment, the apparatus further comprises a signal processing element configured to produce a physiological measurement result using at least one of: an output signal of the first photodetector and an output signal of the second photodetector.

In an example embodiment, the apparatus comprises a plurality of the first photodetectors and a plurality of the second photodetectors.

In an example embodiment, the apparatus is configured to combine output signals of the first photodetectors to form a combined first signal and to combine output signals of the second photodetectors to form a combined second signal.

In an example embodiment, the apparatus is a physiological measurement sensor.

According to a second example aspect, there is provided a user wearable apparatus comprising any apparatus defined in the foregoing.

Different non-binding example aspects and embodiments have been illustrated in the foregoing. The embodiments in the foregoing are used merely to explain selected aspects or steps that may be utilized in implementations according to the present disclosure. Some embodiments may be presented only with reference to certain example aspects. It should be appreciated that corresponding embodiments may apply to other example aspects as well.

BRIEF DESCRIPTION OF THE DRAWINGS

For a more complete understanding of example embodiments of the present disclosure, reference is now made to the following descriptions taken in connection with the accompanying drawings in which.

DETAILED DESCRIPTION OF THE DRAWINGS

Example embodiments of the present disclosure and its potential advantages are understood by referring to FIGS. 1 through 11 of the drawings. In this document, like reference signs denote like parts or steps.

In various example embodiments there is provided a new detector arrangement suited for being used in optical sensors for example for measuring physiological parameters of a subject. Such optical sensors measure physiological parameters of the subject and produce sensor signals corresponding to a property of the matter underlying the skin of the subject (capillaries and veins, for example). The detector arrangement is suited e.g. for user wearable sensor devices.

In the following, various example embodiments are discussed in connection with optical heart rate sensors. Various example embodiments are however not necessarily limited to optical heart rate sensors only. Alternatively or additionally, the example embodiments can be used in optical monitoring of some other physiological parameter, too. Physiological parameters or physiological measurement results referred to herein may include for example one or more of the following: heart rate, respiration rate, blood pressure, oxygen saturation level, and glucose level.

Figure 1:
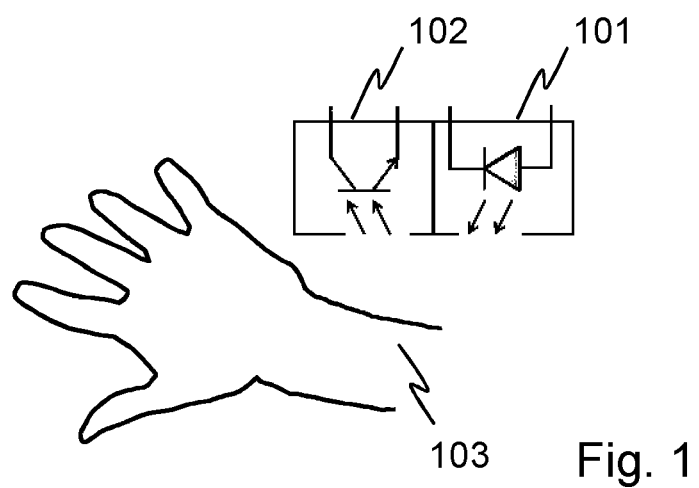
FIG. 1 is a simplified illustration of an example optical heart rate measurement.

Heart rate can be monitored optically by measuring variations in blood volume with a photoplethysmogram (PPG) sensor. FIG. 1 is a simplified illustration of an example optical heart rate sensor. FIG. 1 shows a (reflective type) PPG sensor that comprises a light source 101 and a photodetector 102. The light source in the shown example is a LED (light emitting diode) and the photodetector is a phototransistor. Also a photo diode (PD) may be used. The light source 101 emits light and the photodetector 102 receives light rays reflected from tissue 103 of a subject. The sensor produces sensor signals based on the light detected by the photodetector 102.

In an example embodiment there is provided an apparatus (e.g. an optical sensor) with two or more photodetectors. The photodetectors are configured to concurrently detect light received at the apparatus. In an example embodiment a first photodetector is configured to receive a range of wavelengths and a second photodetector is configured not to receive a target wavelength. In an example embodiment, the target wavelength is a wavelength of interest. The target wavelength may be indicated in terms of a single wavelength, for example 525 nm, but it is understood that the target wavelength may be a narrow wavelength band around the stated wavelength.

According to an example embodiment, the first photodetector and the second photodetector are in a stacked arrangement. The first photodetector is configured to detect a first portion of light and the apparatus is configured to pass a second portion of the light through the first photodetector to the second photodetector. The portion of the light that is passed through may be half of the incident light on the first photodetector whereby the first and second portions may be equal or at least nearly equal. In an example embodiment the portion of the light that is passed through is 45-55% of the light incident on the first photodetector. In an example embodiment, the first photodetector is a conventional photodiode furnished with transparent areas such as holes that allow a portion of the light to pass through. In an example implementation the holes are drilled holes, but also other mechanisms to produce the holes may be used. The holes may be filled with suitable filling material. In another example embodiment, the first photodetector is a semi-transparent organic photodetector or a graphene quantum-dot detector. In an example embodiment the second portion of light is passed through the first photodetector without changing direction of the light. In this way the angle of incidence of incoming light is the same for both the first and the second photodetectors.

It is to be noted that ideally a photodetector fully detects incident light, but in practical implementation a portion of the incident light may leak through the photodetector. It is to be understood that such leakage may exist in the examples of the following disclosure. Therefore a reference to a first photodetector detecting a first portion of light and a second photodetector detecting a second portion of light is to be understood to cover also situations where such leakage may exist.

In an example embodiment, the apparatus comprises an optical blocking filter that is configured to filter the light incident at the second photodetector. The optical blocking filter may be placed in the stacked arrangement between the first photodetector and the second photodetector. The optical blocking filter blocks some wavelengths. The optical blocking filter may be for example a notch filter or a band-stop filter, and may comprise a dichroic mirror. Filters that use dichroic mirrors can be very steep and therefore they may suit well for example embodiments of present disclosure because they enable precise separation of wavelengths. In an example embodiment the optical blocking filter is configured to block a target wavelength, which is the wavelength of interest in. In an ideal implementation the optical blocking filter blocks 100% of the target wavelength. It is however understood that in practical implementations a minimal amount of the target wavelength may leak through the optical blocking filter. It is understood that blocking covers also situations where such leakage may exist. In this way, the second photodetector does not receive the target wavelength. In an example embodiment the target wavelength is 525 nm wavelength (green light), 650 nm wavelength (red light) or 950 nm wavelength (infrared light), but other wavelengths can be equally used.

In an example embodiment there are more than one optical blocking filters. For example a first optical blocking filter may block 525 nm light (or some other visible light wavelength) and a second optical blocking filter may block infrared light. The optical blocking filters may be arranged in a stacked configuration in which they may be in contact with each other.

In an example embodiment, the apparatus comprises an angle adjustment element that is configured to adjust the angle of light received at the apparatus. In general the angle adjustment element is an element that affects the angle of light that passes through the element. The angle adjustment element may be an angle-limiting filter that is configured to block light rays with undesired angle of incidence or it may be a collimator configured to change direction of arriving light rays so that the light rays exiting or passing through the collimator have a desired angle. It is to be understood that the angle adjustment element is not a mandatory element even though an angle adjustment element is included by way of example in many of the example embodiments discussed herein.

In an example embodiment, the apparatus comprises a light source that emits light at a wavelength that may be the target wavelength. The blocking filter matches the wavelength of the light source. That is, the optical blocking filter is configured to filter out the wavelength of the light source.

Now, when the first and second photodetectors detect light, the second photodetector (which does not receive the target wavelength) can be considered to detect only unwanted wavelengths. The detected light signals may be subtracted from each other to produce a result signal that is cleared from noise and artifacts originating from the unwanted wavelengths. In an example embodiment there is provided an analog circuit configured to perform the subtraction. In another alternative the detected signals are analog-to-digital converted and then subtracted digitally. The resulting signal may then be used for producing a physiological measurement result, such as heart rate. Additionally, the signals detected by the first and second photodetectors may be used as such, i.e. without being subtracted from each other, for producing physiological measurement results.

Figure 2:
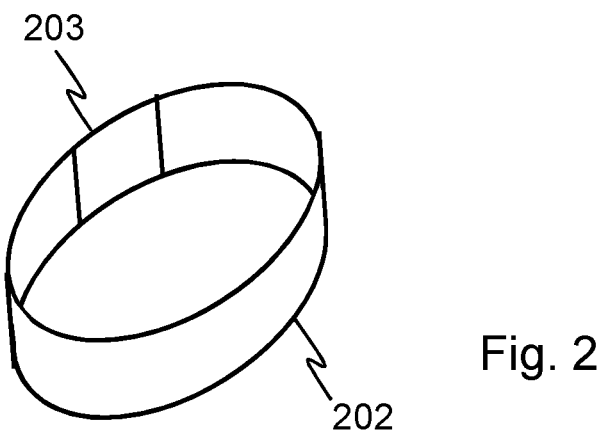
FIG. 2 is a simplified illustration of an example user wearable sensor device.

FIG. 2 is a simplified illustration of an example sensor 203 wherein example embodiments may be implemented. The sensor 203 is attached to a strap 202 that allows the sensor 203 to be fitted for example around a wrist of a subject.

The casing of the sensor 203 can be made of a suitable material, such as a plastics material (e.g. acrylonitrile butadiene styrene (ABS) or polycarbonate (PC)), carbon fiber materials, glass, wood, metal, ceramics, fabric, leather or any combination of these. The strap 202 may be made of suitable flexible material, such as plastic, fabric, and leather. In an example embodiment, the strap 202 and the casing of the sensor 203 are integrally formed of one piece of material. The material can comprise or consist for example of any of the following: plastics, metals, nano-fibers, carbon fiber, leather, fabric and glass.

FIG. 2 shows the sensor 203 attached to a strap 202, but the sensor may equally be part of some other user wearable apparatus that can be fitted around or attached to a body part (e.g. wrist, ankle or finger) of a user. The sensor 203 may be configured to be integrated into a garment of a subject. The sensor may be attached or integrated for example to a belt, a sock, a shoe, a sleeve or a collar of a shirt or pullover, and/or a waistband of trousers or skirt. The sensor may be detachable from the garment. The sensor may be shaped like a watch and it may be configured to display time or other useful information to the user. The sensor may be attached to a patch or to a plaster (with adhesive) or to a ring. A further alternative is that the sensor is attached to an ear of the user. The sensor may be part of an earplug, for example.

Figure 3:
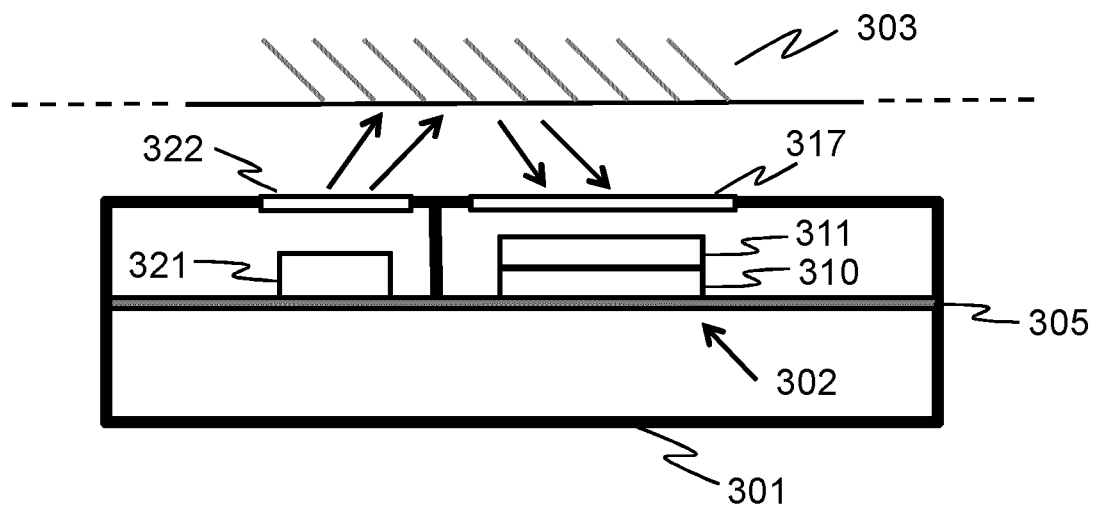
FIGS. 3-6 are cross sectional views of detector arrangements of example embodiments.

FIGS. 3-6 are cross sectional views of detector arrangements of example embodiments. FIG. 3 shows tissue 303 of a subject and an apparatus 301 comprising a printed circuit board (PCB) 305, a detector arrangement 302, and a light source 321. Further there is a window element 322 that allows light emitted by the light source 321 to exit the apparatus 301 and a window element 317 that allows light to be received by the apparatus 301. It is to be noted that the window elements 322 and 317 are not mandatory. Instead the apparatus 301 may comprise apertures that allow light to exit and enter the apparatus 301. The detector arrangement 302 comprises a first photodetector 311 and a second photodetector 310 in a stacked arrangement. The first photodetector 311 is partially transparent and passes through a portion of the light incident on the first photodetector 311.

In an example embodiment, the apparatus 301 of FIG. 3 operates as follows: The light source 321 emits light through the window element 322. The light is reflected from the tissue 303 of the subject and the light enters the detector arrangement 302 through the window element 317. The first photodetector 311 detects a first portion of the light and passes through a second portion of the light to the second photodetector 310. The second photodetector 310 detects the second portion of the light. Further there is an optical blocking filter (not shown in FIG. 3) between the first and the second photodetectors to filter the light that passes through the first photodetector prior to the light arriving at the second photodetector 310.

The first photodetector 311 detects all wavelengths of the light rays that are received at the detector arrangement. The second photodetector 310 detects all other wavelengths of the light except the wavelength blocked by the optical blocking filter. The first photodetector 311 produces a first detected signal and the second photodetector 310 produces a second detected signal. These detected signals may then be used for providing physiological measurement signals.

Figure 4:
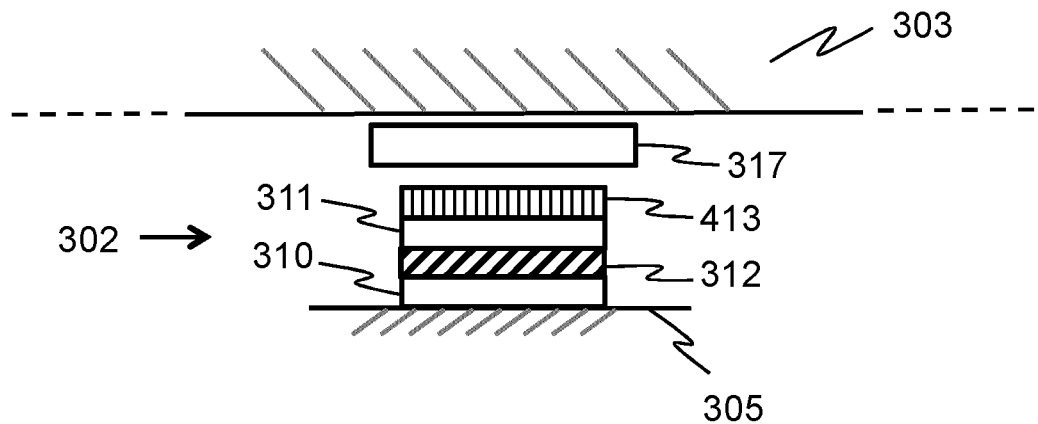

FIG. 4 shows a detector arrangement 302 comprising a window element 317 and a detector stack on a PCB 305. The detector stack comprises an angle adjustment element 413, a first photodetector 311, an optical blocking filter 312, and a second photodetector 310 in a stacked arrangement.

In an example embodiment, the example detector arrangement of FIG. 4 operates as follows: Light is received through the window element 317. The angle adjustment element 413 may adjust the angle of arrival of the light. The first photodetector 311 detects a first portion of the light and passes through a second portion of the light to the optical blocking filter 312 between the first and the second photodetectors 311 and 310. The optical blocking filter 312 filters the second portion of light and the filtered second portion of light arrives at the second photodetector 310.

The first photodetector 311 produces a first detected signal and the second photodetector 310 produces a second detected signal. These detected signals may then be used for providing physiological measurement signals.

Figure 5:
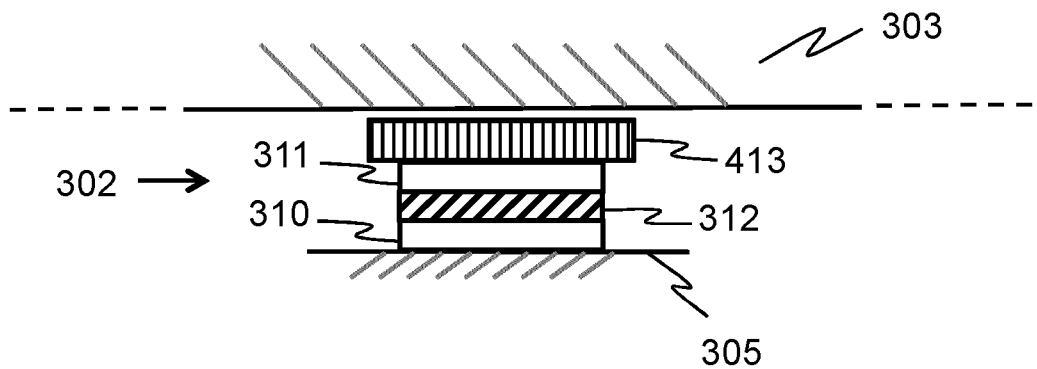

FIG. 5 shows a detector arrangement 302 where the angle adjustment element 413 is integrated into the window element. There is a detector arrangement 302 comprising a detector stack on a PCB 305. The detector stack comprises the angle adjustment element 413, a first photodetector 311, an optical blocking filter 312, and a second photodetector 310 in a stacked arrangement.

In an example embodiment, the example detector arrangement of FIG. 5 operates as follows: Light is received through the angle adjustment element 413 that may adjust the angle of arrival of the light. The first photodetector 311 detects a first portion of the light and passes through a second portion of the light to the optical blocking filter 312 between the first and the second photodetectors 311 and 310. The optical blocking filter 312 filters the second portion of light and the filtered second portion of light arrives at the second photodetector 310.

The first photodetector 311 produces a first detected signal and the second photodetector 310 produces a second detected signal. These detected signals may then be used for providing physiological measurement signals.

Figure 6:
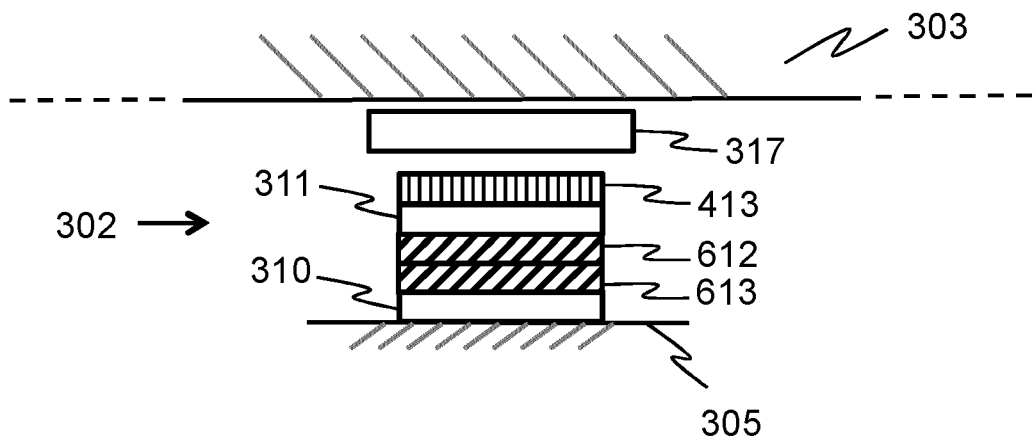

FIG. 6 shows a detector arrangement 302 with two optical blocking filters in a stacked arrangement. The detector arrangement 302 comprises a window element 317 and a detector stack on a PCB 305. The detector stack comprises an angle adjustment element 413, a first photodetector 311, a first and a second optical blocking filters 612 and 613, and a second photodetector 310 in a stacked arrangement.

In an example embodiment, the example detector arrangement of FIG. 6 operates as follows: Light is received through the window element 317. The angle adjustment element 413 may adjust the angle of arrival of the light. The first photodetector 311 detects a first portion of the light and passes through a second portion of the light to the first optical blocking filter 612 in the stacked arrangement. The first optical blocking filter 612 filters the second portion of light and the filtered second portion of light arrives at the second optical blocking filter 613 in the stacked arrangement. The second optical blocking filter 613 filters the light filtered by the first optical blocking filter and the twice filtered second portion of light arrives at the second photodetector 310.

The first photodetector 311 produces a first detected signal and the second photodetector 310 produces a second detected signal. These detected signals may then be used for providing physiological measurement signals.

A dual wavelength detector may be provided with the example detector arrangement of FIG. 6. In an example embodiment there are two light sources having wavelengths different from each other (not shown in FIG. 6). The first optical blocking filter is configured to filter out the wavelength of one of the light sources and the second optical blocking filter is configured to filter out the wavelength of the other light source.

Such dual wavelength detector may be used in pulse oximetry measurement for oxygen saturation (SpO2) measurement. There may be for example a red light source (650 nm) and an infrared light source (950 nm) and corresponding optical blocking filters. In an alternative implementation there may be a 560 nm green light source and a 577 nm green light source and corresponding optical blocking filters.

In an example embodiment a sequential measurement is done so that the light sources are illuminated sequentially and corresponding detected signals are recorded sequentially. I.e. measurement using the red light source and the infrared light source are performed sequentially with the same detector arrangement.

It is to be noted that in stacked arrangements of example embodiments, there may be arranged an air gap or suitable filling material between at least some of the elements of the detector arrangement. For example, there may be an air gap between a window element and the detector stack. Additionally or alternatively there may be transparent substrate between at least some of the layers of the detector stack.

Figure 7:
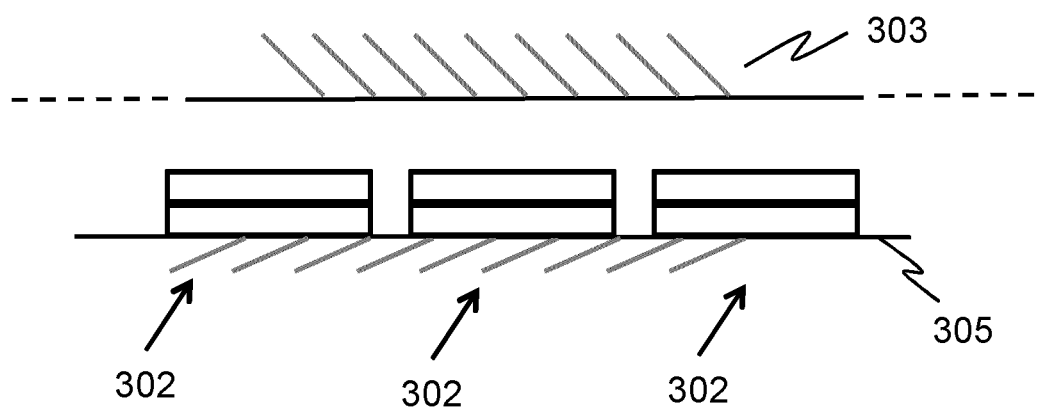
FIG. 7 is cross sectional view illustrating another example embodiment.

FIG. 7 is a schematic drawing illustrating yet another example embodiment comprising a plurality of detector arrangements 302 each comprising a first photodetector and a second photodetector. The detector arrangements 302 of FIG. 7 may comprise the internal structure of one of the example embodiments shown in FIGS. 3-6. Three detector arrangements 302 are shown in FIG. 7. Additionally FIG. 7 shows PCB 305 and tissue 303 of a subject. The detector arrangements 302 may be configured to detect light reflected from the tissue 303.

It is to be understood that the number of detector arrangements 302 is not limited.

In an example embodiment the signals detected by the photodetectors of the detector arrangements are processed so that signals detected by first photodetectors of different detector arrangements are combined and signals detected by second photodetectors of different detector arrangements are combined. The resulting signals may then be subtracted or used as such for producing physiological measurement signals.

Figure 8:
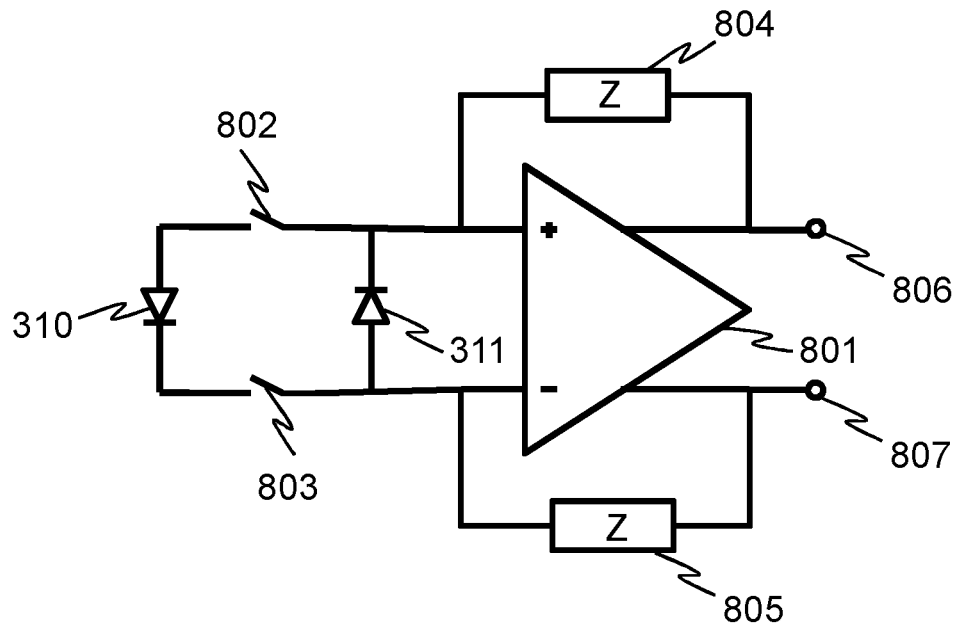
FIGS. 8-10 are circuit diagrams of example embodiments.
Figure 9:
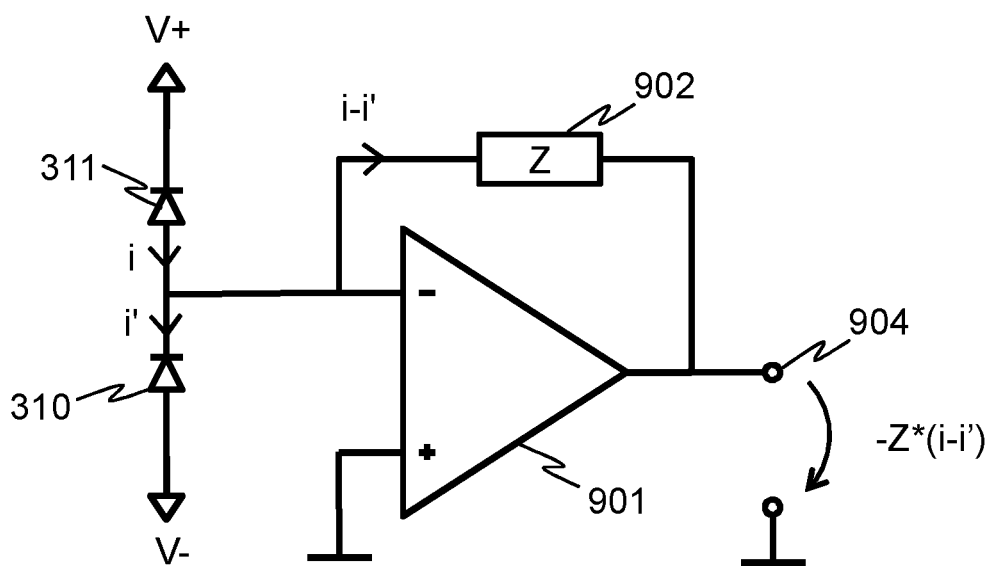
Figure 10:
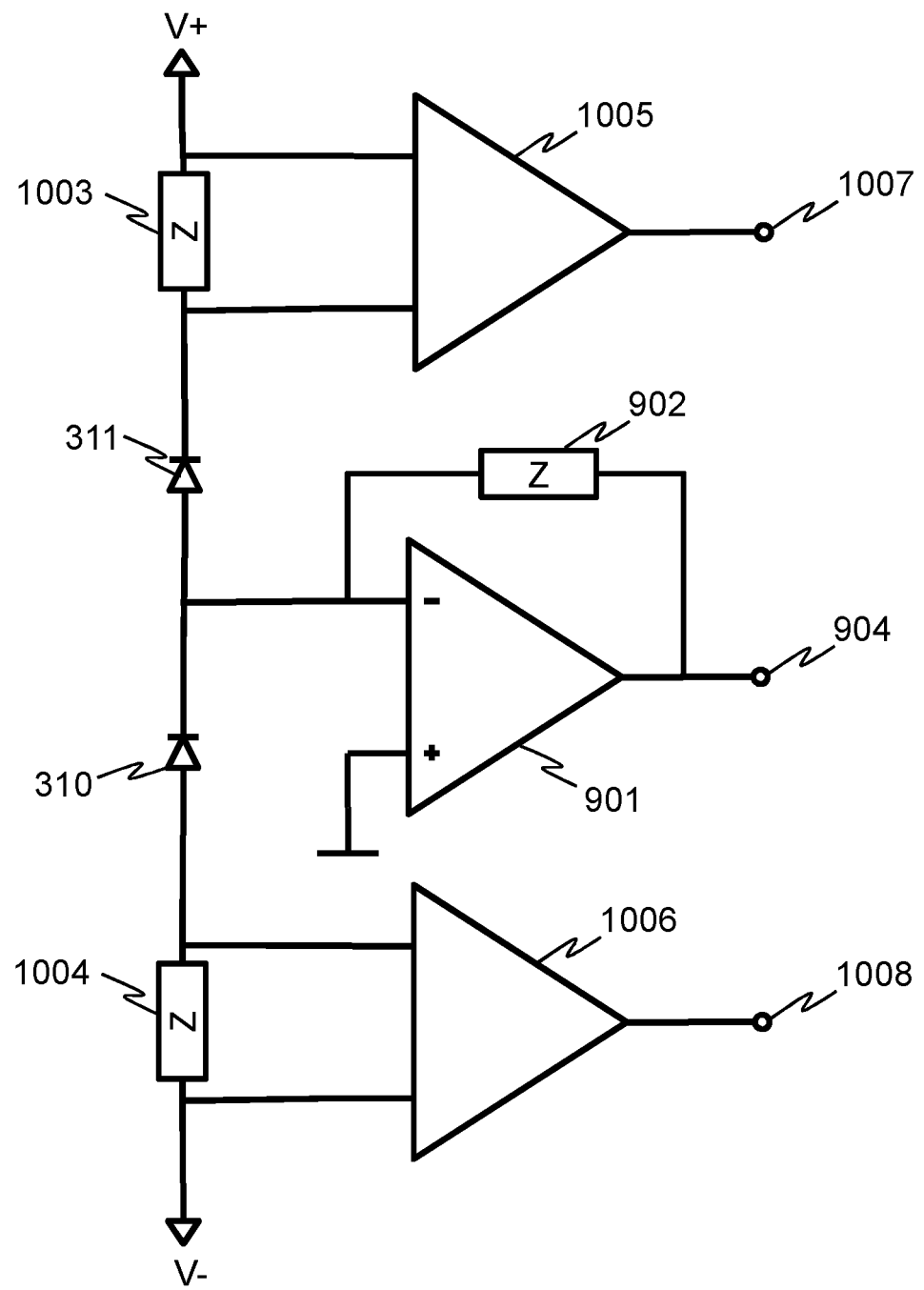

FIGS. 8-10 are circuit diagrams of example embodiments. The shown examples comprise a first photodetector 311 and a second photodetector 310. In an example embodiment the first photodetector 311 is configured to receive a range of wavelengths and the second photodetector 310 is configured not to receive a target wavelength. In an example embodiment the second photodetector detects light that is filtered with an optical blocking filter. The optical blocking filter is not shown in FIGS. 8-10.

The circuit of FIG. 8 comprises amplifier 801, impedances 804 and 805 and switches 802 and 803 in addition to the first photodetector 311 and the second photodetector 310. The first and second photodetectors 310 and 311 are arranged in parallel connection with opposite polarities. That is, the photodetectors are connected back-to-back in parallel. The switches 802 and 803 are operable to couple or uncouple the second photodetector to the amplifier 801. In this way the arrangement may be operated as a detection circuitry in which only the first photodetector is coupled to the amplifier 801, or as a detection circuitry with analog motion artifact cancellation when both the first and second photodetectors are coupled to the amplifier 801. When both the first and the second photodetector are coupled to the amplifier, voltage over the output terminals 806 and 807 of the amplifier 801 is representative of the difference between light detected by the first photodetector 311 and the second photodetector 310.

FIG. 9 shows a single-ended circuit. The circuit comprises the first photodetector 311 and the second photodetector 310, impedance 902 and an amplifier 901. As an output 904 the circuit of FIG. 9 provides voltage representative of the difference between the light detected by the first photodetector 311 and the second photodetector 310.

FIG. 10 shows yet another circuit comprising the first photodetector 311 and the second photodetector 310, amplifiers 901, 1005 and 1006, and impedances 902, 1003 and 1004.

The circuit of FIG. 10 provides three outputs 904, 1007, 1008. Output 1007 provides voltage representative of the light detected by the first photodetector 311, output 1008 provides voltage representative of the light detected by the second photodetector 310, and output 904 provides voltage representative of the difference between the light detected by the first photodetector 311 and the second photodetector 310. In practical implementations, the output 1008 and related components may not be needed, as there may be less interest in processing solely the signal from the second photodetector 310.

Figure 11:
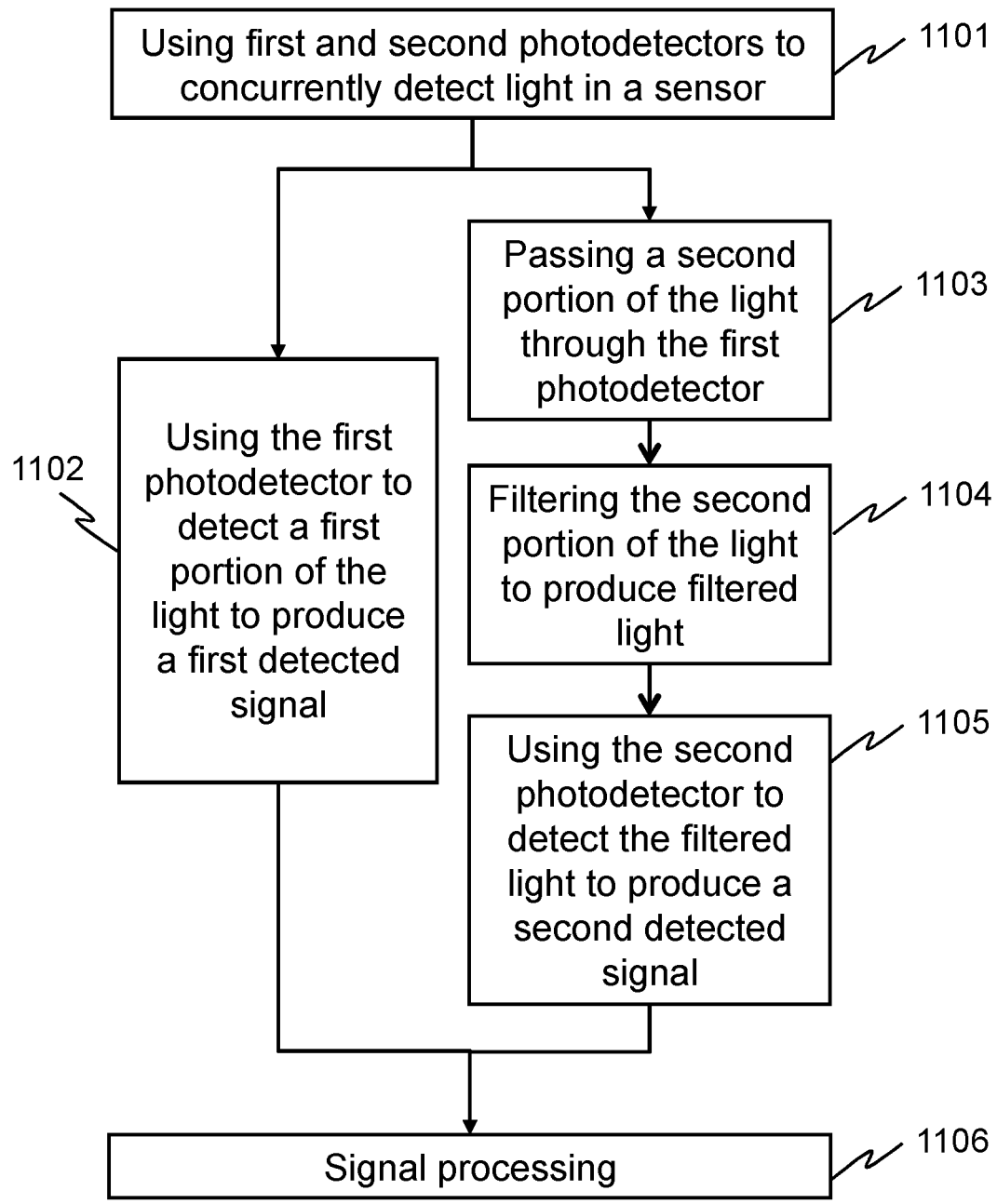
FIG. 11 is a flow chart of a process of an example embodiment.

FIG. 11 shows a flow chart of a process of an example embodiment. The process comprises:

1101: A first and a second photodetector are used to concurrently detect light in a sensor, such as a physiological measurement sensor. The sensor may be e.g. an optical heart rate sensor.

1102: The first photodetector detects a first portion of the light and produces a first detected signal.

1103: A second portion of the light is passed through the first photodetector.

1104: The second portion of the light is filtered to produce filtered light. The filtering is performed e.g. using an optical blocking filter, such as a dichroic mirror. In different example embodiments there may be one or more filters that filter the light prior to the light arriving at the second photodetector.

1105: The second photodetector detects the filtered light and produces a second detected signal.

1106: The first and second detected signals are processed to produce physiological measurement results. In an example embodiment the second detected signal is subtracted from the first detected signal in an analog circuit and the result is analog-to-digital converted. The physiological measurement results are then produced in digital domain.

Without in any way limiting the scope, interpretation, or application of the claims appearing below, a technical effect of one or more of the example embodiments disclosed herein is that an improved optical detector arrangement is provided. The detector arrangement of example embodiments provides that the angle of incidence of incoming light is the same for both the first and the second photodetectors. This eliminates or at least reduces effects of angular dependency of the response of the first and second photodetectors. In this way the first and second photodetectors produce comparable detected signals. Thus, accuracy of noise cancellation that uses signals from both the first and the second photodetectors may be improved. Thereby, accuracy of overall measurement may be improved.

Another technical effect of one or more of the example embodiments disclosed herein is that analog noise cancellation is enabled. Analog noise cancellation may be faster and more robust than digital solutions. A benefit of analog noise cancellation is that it is directed to removing or reducing the component causing inaccuracies in measurement signal (i.e. removing the original cause) instead of trying to improve interpretation of the inaccurate measurement signal. In this way one may achieve that a need to develop and use complex software algorithms to correct the measurement signal may be reduced. Instead simpler algorithms may be applied.

Another technical effect of one or more of the example embodiments disclosed herein is that DC component of a measured signal is reduced. In heart rate monitoring applications DC is not an interesting component and the presence of the DC component only narrows down the effective dynamic range of an analog front-end.

Another technical effect of one or more of the example embodiments disclosed herein is that the solution is easy to take into use. Various example solutions are compatible with existing optical measurement ICs (integrated circuits) and/or can be easily made compatible with existing optical measurement ICs.

Another technical effect of one or more of the example embodiments disclosed herein is that the solution is less sensitive to ambient and other unwanted light sources. Another technical effect of one or more of the example embodiments disclosed herein is that a wide spectrum light source can be used. For example wider spectrum than spectrum provided by LEDs could be used.

If desired, the different functions discussed herein may be performed in a different order and/or concurrently with each other. It is understood that desired features from one explicitly disclosed example embodiment may be combined with a selection of features from other example embodiments.

Although various aspects of present disclosure are set out in the independent claims, other aspects of the present disclosure comprise other combinations of features from the described example embodiments and/or the dependent claims with the features of the independent claims, and not solely the combinations explicitly set out in the claims.

It is also noted herein that while the foregoing describes example embodiments, these descriptions should not be viewed in a limiting sense. Rather, there are several variations and modifications, which may be made without departing from the scope of the present disclosure as defined in the appended claims.

The invention claimed is:

1. An apparatus comprising:
   a first photodetector and a second photodetector, where each of the first photodetector and the second photodetector is configured to detect a similar range of wavelengths, wherein the apparatus is configured to receive light,
   the first photodetector is configured to detect a first portion of the light, and
   the first photodetector and the second photodetector are in a stacked arrangement and the apparatus is configured to pass a second portion of the light through the first photodetector to the second photodetector, the apparatus comprising
   an optical blocking filter configured to filter the second portion of the light prior to the second portion of the light arriving at the second photodetector;
   wherein the optical blocking filter is configured to block a portion of the second portion of the light of a target wavelength.

2. The apparatus of claim 1, wherein the first photodetector is configured to detect the first portion of light having a first magnitude and the second photodetector is configured to detect the second portion of light having a second magnitude that is substantially equal to the first magnitude of the first portion of light.

3. The apparatus of claim 1, wherein the second photodetector is configured to detect 45-55% of light incident on the first photodetector as the second portion of light.

4. The apparatus, of claim 1, wherein the first photodetector comprises semi-transparent material.

5. The apparatus of claim 1, wherein the first photodetector comprises holes, which allow the second portion of the light to pass through the first photodetector.

6. The apparatus of claim 1, wherein the first photodetector is configured to pass the second portion of light through the first photodetector without changing direction of the light.

7. The apparatus of claim 1, wherein the optical blocking filter is a notch filter.

8. The apparatus of claim 1, further comprising
   a light source configured to emit light at the target wavelength.

9. The apparatus of claim 1, wherein the optical blocking filter comprises at least one second optical blocking filter, the optical blocking filter and the at least one second optical blocking filter being arranged in a stacked arrangement.

10. The apparatus of claim 1, further comprising an angle adjustment element configured to adjust the angle of incidence of the light prior to the light arriving at the first photodetector.

11. The apparatus of claim 1, further comprising analog circuitry configured to subtract an output signal of the second photodetector from an output signal of the first photodetector.

12. The apparatus of claim 1, further comprising a signal processing element configured to produce a physiological measurement result using at least one of: an output signal of the first photodetector and an output signal of the second photodetector.

13. The apparatus of claim 1, wherein the apparatus comprises a plurality of the first photodetectors and a plurality of the second photodetectors, and wherein the apparatus is configured to combine output signals of the first photodetectors to form a combined first signal and to combine output signals of the second photodetectors to form a combined second signal.

14. The apparatus of claim 1, wherein the apparatus is a physiological measurement sensor.

* * * * *